US00PP08050P

United States Patent [19]

Zampini

[11] Patent Number: Plant 8,050

[45] Date of Patent: Dec. 1, 1992

[54] ORNAMENTAL PEAR TREE NAMED VALZAM

[75] Inventor: James W. Zampini, 5052 S. Ridge Rd., Perry, Ohio 44081-0122

[73] Assignee: James W. Zampini, Perry, Ohio

[21] Appl. No.: 630,546

[22] Filed: Dec. 20, 1990

[51] Int. Cl.[5] ..... A01H 5/00

[52] U.S. Cl. ..... Plt./36

[58] Field of Search ..... Plt./36

[56] References Cited

U.S. PATENT DOCUMENTS

P.P. 2,489 3/1965 Seanlon ..... Plt. 36
P.P. 3,815 12/1975 Flemer ..... Plt. 36
P.P. 4,591 9/1980 Westwood ..... Plt. 36

OTHER PUBLICATIONS

Anon. *Wholesale Price List,* Princeton Nurseries, N.J., (1988–1989) pp. 76–79.

*Primary Examiner*—James R. Feyrer
*Attorney, Agent, or Firm*—Burns, Doane, Swecker & Mathis

[57] ABSTRACT

A new and distinct variety of ornamental pear tree named Valzam is provided. The new variety can be readily distinguished from the Cleveland Select variety of callery pear tree (nonpatented in the United States). For instance, the new variety is shorter in stature with a more compact branching structure having less scaffolding, generally forms lateral branches having a larger diameter, forms lateral branches leaving the tree at a lesser angle giving the tree a more pyramidal form, and forms larger and darker leaves which turn a brighter and more intense shade of red approximately two weeks earlier. The new variety is particularly well suited for growing as attractive ornamentation and/or for shade purposes in the landscape.

3 Drawing Sheets

SUMMARY OF THE INVENTION

The new and distinct variety Pyrus ornamental pear tree was discovered during 1975 as a seedling of unknown parentage while growing in a cultivated area tended by man. More specifically, the new variety was discovered while growing among trees of the Cleveland Select variety of *Pyrus calleryana* being grown on the Kohankie Farm located at Perry, Ohio in Zone 6*a*. The seed parent of the new variety is believed to be the Cleveland Select variety of *Pyrus calleryana* and the pollen parent is unknown.

My attention was initially attracted to a single plant of the new variety since it was found to exhibit a combination of characteristics which differ significantly from those of the Cleveland Select variety of ornamental pear tree. Had I not discovered and preserved this new tree it would have been lost to mankind.

It has been found that the new and distinct flowering callery pear tree of the present invention exhibits the following combination of characteristics when compared to the Cleveland Select variety of *Pyrus calleryana:*

(a) exhibits a shorter overall stature,
(b) exhibits a more compact branching structure with less branch scaffolding,
(c) generally forms lateral branches having a larger diameter at an earlier age,
(d) forms lateral branches which leave the tree at a lesser angle thereby giving the tree a more upright and pyramidal form,
(e) forms leaves that are larger and darker, and
(f) forms autumn foliage which turns color approximately two weeks earlier and exhibits a brighter and more intense red coloration.

Trees of the new variety have been asexually reproduced by T-budding onto *Pyrus calleryana* understocks.

The characteristics of the new variety have been found to be strictly transmissible by such asexual propagation from one generation to another.

The new variety has been named the VALZAM variety. Also, trees of the new variety are being marketed of Perry, Ohio, under the VALIANT trademark.

BRIEF DESCRIPTION OF THE PHOTOGRAPHS

The accompanying photographs show as nearly true as it is reasonably possible to make the same in color illustrations of this character, typical specimens of the tree and plant parts of the new variety. The specimens depicted were grown at Perry, Ohio.

Figure 1:
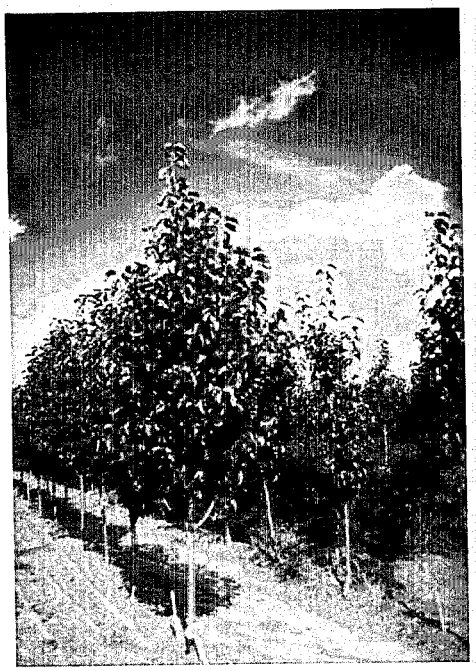
FIG. 1 illustrates a five year old tree of the new variety at the beginning of the fall season.
Figure 2:
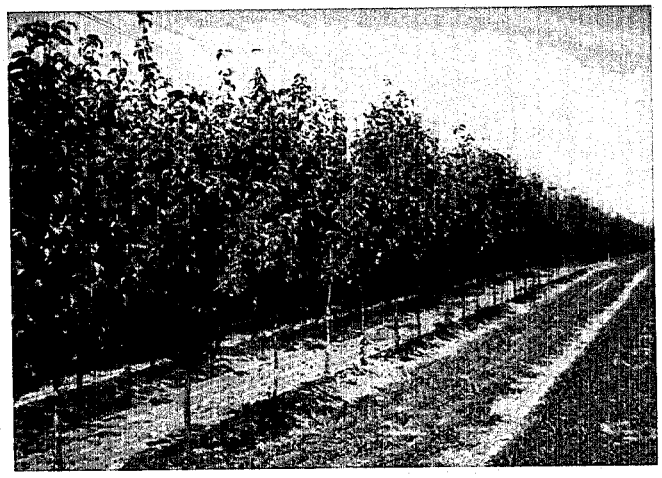
FIG. 2 illustrates a row of five year old trees of the new variety exhibiting fall coloration earlier than other *Pyrus calleryana* cultivars shown in the background.
Figure 3:
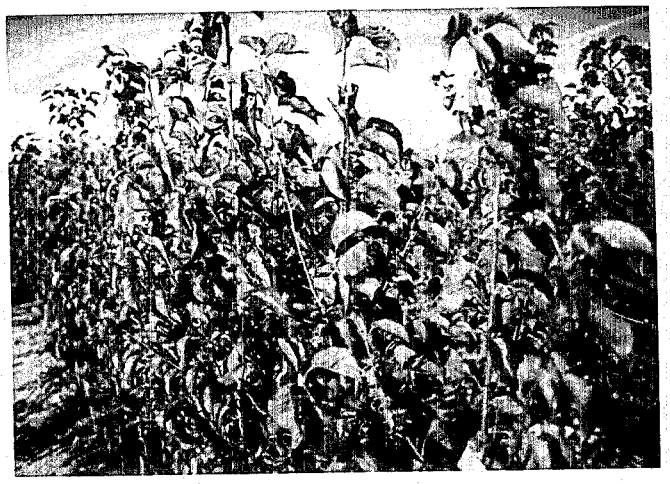
FIG. 3 illustrates a row of the new variety showing its usual fall coloration. High winds account for the lighter colored undersides of the leaves; however, the dark red upper surfaces of the leaves are visible, particularly in the foreground.
Figure 4:
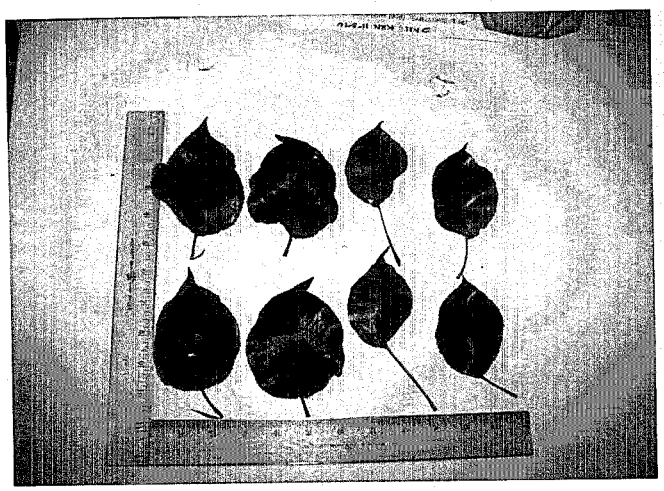

FIG. 4 illustrates for comparative purposes four representative leaves of the new variety on the left and four representative leaves of the Cleveland Select ornamental pear variety on the right. The photograph was made during early November thus one was able to obtain both green and fall-colored foliage. The disparity in leaf size and color is apparent.

Figure 5:
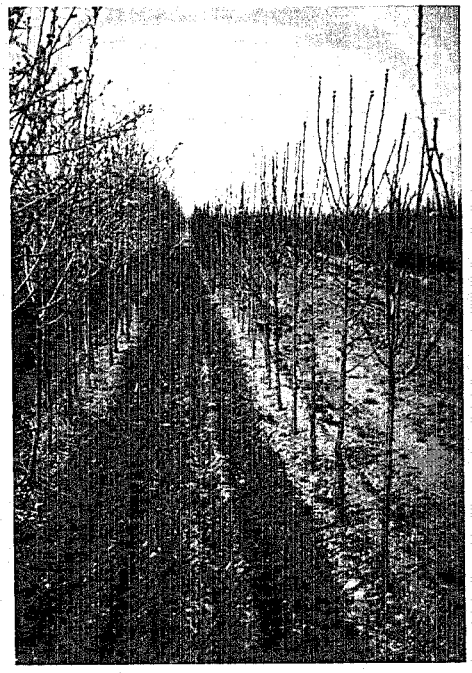

FIG. 5 illustrates a row of four year old trees of the new variety on the right during the winter season showing less scaffold branching and lesser branch angling compared to the *Pyrus calleryana* selection on the left.

Figure 6:
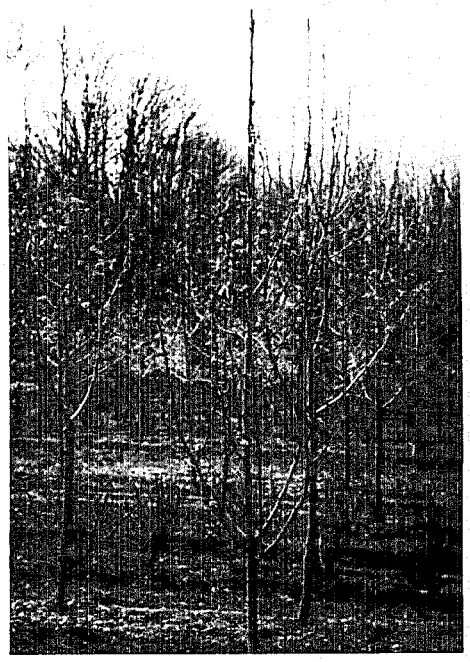

FIG. 6 illustrates a four year old tree during the winter season.

DETAILED DESCRIPTION

The chart used in the identification of colors is that of the Royal Horticultural Society (R.H.S. Colour Chart). Other references to color are to be accorded their ordinary dictionary significance. The descriptions are based upon trees grown at Perry, Ohio.

The original tree of the new variety exhibits an overall shorter growth habit than the Cleveland Select variety and presently is approximately 25 feet tall, approximately 15 feet wide and has a caliper of approximately 7 inches at grade. Accordingly, the new variety exhibits a more compact branching structure with less branch scaffolding than the Cleveland Select variety. When grown on its own roots, the tree is expected to reach a height of approximately 25 to 30 feet and a width of approximately 15 to 20 feet at full maturity as opposed to the Cleveland Select variety which is expected to reach a height of approximately 30 to 35 feet an a width of approximately 20 feet at full maturity.

The new variety when compared to the Cleveland Select variety of *Pyrus calleryana* has been found to form lateral branches which are larger in diameter at an earlier age and which leave the tree at a lesser angle creating a more upright and pyramidal form. For instance, the branches of the Cleveland Select variety commonly leave the tree at angle of approximately 45 degrees while the branches of the new variety commonly leave the tree at an angle of approximately 30 degrees.

As is common with many callery pear cultivars, the new variety forms a central leader. However, due to the branching structure, such central leader readily is challenged by secondary branches. The new variety tends to produce as dense a canopy with fewer branches but larger leaves when compared to the Cleveland Select variety. This characteristic would lead one to believe that the pruning and training requirements for the new variety accordingly are reduced.

When compared to the Cleveland Select variety, the new variety is considered to be of comparable vigor, but forms a tree having an overall smaller size. Instead of forming a tree having a height and width comparable to that of the Cleveland Select variety, the new variety tends to direct into its energies into the formation of sturdy branches having a greater girth than those of the Cleveland Select variety. No thorns have been observed on trees of the new variety to date.

The blossom appearance of the new variety is similar to the Cleveland Select variety of *Pyrus calleryana.* The present variety forms in profusion attractive white blossoms which generally correspond to White Group 155D. The flowering commonly begins before leaf break.

The configuration of the flowers is generally typical of the genus, and in particular of that of the Cleveland Select variety of ornamental pear tree. The flowers are perfect, single and extremely numerous. Blooming commonly occurs from early April to early May at Perry, Ohio where it commonly occurs for approximately 10 days depending upon the weather conditions. Such flowers are commonly borne in 3 inch diameter corymbs on glabrous to tomentose pedicles having a length of approximately ⅜ to ½ inch. The individual blossoms commonly average approximately ½ inch in diameter at the broadest point when fully expanded. The corolla consists of 5 obovate petals. The new variety produces pollen which is believed to be self-fertile.

The vegetative and reproductive parts of the new variety are in most respects typical of the genus, and in particular of that of the Cleveland Select variety of ornamental pear tree. The leaves are usually alternate, simple and broadly-ovate and tend to be larger than those of the Cleveland Select variety of ornamental pear tree as illustrated. The leaf coloration during mid-season commonly approximates that of Green Group 137A on the upper surface and tends to be somewhat paler on the under surface. The leaves have a generally rounded base and commonly end in an acuminate tip. The leaf margins are crenate. The leaves mature to a glabrous, leathery, lustrous, dark green coloration. The leaves of vegetative shoots commonly reach a length of approximately 4 to 5 inches and include a petiole commonly measuring approximately 1 inch in length. The leaves of fruiting shoots tend to be smaller in size and variable in all dimensions. The immature twigs are glabrous, smooth and of an olive green coloration with small orange lenticels which persist with age. Two-year old twigs tend to be of a darker olive green coloration. Branches mature to shades of substantially the same coloration as the autumn foliage and tend to display a more pronounced coloration on the upper portions of the branches. Winter buds are generally approximately ½ inch long and commonly possess tomentose scales.

The new variety has been found to begin its autumn leaf coloration approximately two weeks earlier than the Cleveland Select variety of *Pyrus calleryana.* For instance, it starts exhibiting shades of crimson beginning in mid-October at Perry, Ohio. The peak leaf coloration during the autumn months approximates Greyed-Purple Group 187A on the upper surface as opposed to the coloration of the Cleveland Select variety which approximates Greyed-Red Group 178A.

Immature twigs are glabrous, smooth and of an olive green coloration with slender irregularly rounded lenticles that possess an orange coloration. Second year wood is a darker olive green and possesses irregularly rounded orange lenticles. Branches mature to shaded of substantially the same coloration as the foliage in the autumn, and display more pronounced coloration on the upper portions of the branches.

The fruit of the new variety is of a brownish-tan coloration. The fruit is a rounded pome which is densely russet-dotted and borne on stiff stalks which are approximately 1½ to 2 inches in length. Such fruit averages approximately ½ inch in diameter. The calyx is deciduous. The quantity of fruit borne on the new variety commonly is approximately 20 percent less than that found on the Cleveland Select variety. This is believed to be attributable to a lesser number of flowers due to the lesser number of scaffold branches which are presented. Typically two seed cells occur in the fruit which contain two seeds per cell. The appearance of the seeds generally corresponds to that of the species. The fruit of the new variety tends to hang on the tree into the winter and eventually drops to the ground. While some fruit may be taken by wildlife, it appears not to be particularly attractive to wildlife and accordingly is generally comparable to other Pyrus plants in this regard.

When grown at Perry, Ohio, the new variety has exhibited disease resistance and has not been affected to any degree by common Pyrus diseases or insects. The new variety has proven to be hardy when grown in Zone 4. For example, on Jan. 21, 1985, it was exposed to a low temperature of −18° F. without a deleterious impact. Also, considerable drought resistance has been exhibited by the new variety. For instance, the average annual precipitation at Perry, Ohio is understood to be 35.4 inches. In two out of the last four years the area has experienced severe drought conditions. In 1988 the annual precipitation was only 29.69 inches and in 1991 the annual precipitation was only 32.67 inches. The new variety withstood these conditions without any known damage.

I claim:

1. A new and distinct variety of flowering ornamental pear tree which exhibits the following combination of characteristics when compared to the Cleveland Select variety of *Pyrus calleryana:*

(a) exhibits a shorter overall stature,
(b) exhibits a more compact branching structure with less branch scaffolding,
(c) generally forms lateral branches having a larger diameter at an earlier age,
(d) forms lateral branches which leave the tree at a lesser angle thereby giving the tree a more upright and pyramidal form,
(e) forms leaves that are larger and darker, and
(f) forms autumn foliage which turns color approximately two weeks earlier and exhibits a brighter and more intense red coloration;

substantially as herein shown and described.

* * * * *